(12) United States Patent
Li et al.

(10) Patent No.: US 11,585,786 B2
(45) Date of Patent: Feb. 21, 2023

(54) HIGH-FREQUENCY MAGNETOIMPEDANCE TESTING APPARATUS AND METHOD

(71) Applicants: Inner Mongolia University of Technology, Hohhot (CN); Shandong University, Shandong (CN)

(72) Inventors: Ze Li, Hohhot (CN); Jingshun Liu, Hohhot (CN); Guanyu Cao, Hohhot (CN); Rui Liu, Hohhot (CN); Shuqin Xiao, Jinan (CN)

(73) Assignees: Inner Mongolia University of Technology, Hohhot (CN); Shandong University, Jinan (CN)

( * ) Notice: Subject to any disclaimer, the term of this patent is extended or adjusted under 35 U.S.C. 154(b) by 265 days.

(21) Appl. No.: 17/141,779

(22) Filed: Jan. 5, 2021

(65) Prior Publication Data
US 2022/0137000 A1    May 5, 2022

(30) Foreign Application Priority Data
Nov. 3, 2020  (CN) .......................... 202011208839.6

(51) Int. Cl.
| | |
|---|---|
| G01N 27/72 | (2006.01) |
| G01N 33/20 | (2019.01) |
| H01R 13/646 | (2011.01) |
| G06F 13/42 | (2006.01) |

(52) U.S. Cl.
CPC ............ *G01N 27/72* (2013.01); *G01N 33/20* (2013.01); *G06F 13/4282* (2013.01); *H01R 13/646* (2013.01); *G06F 2213/0002* (2013.01)

(58) Field of Classification Search
CPC .... G01N 27/72; G01N 33/20; G06F 13/4282; G06F 2213/0002; H01R 13/646; G01R 33/1253
See application file for complete search history.

(56) References Cited

U.S. PATENT DOCUMENTS

| | | | | |
|---|---|---|---|---|
| 6,958,603 | B2 * | 10/2005 | Kondo ................... | G01V 3/104 324/239 |
| 2008/0211492 | A1 * | 9/2008 | Tsukada ............... | G01R 33/063 324/234 |
| 2021/0181273 | A1 * | 6/2021 | Liu ...................... | G01R 33/063 |

* cited by examiner

*Primary Examiner* — Giovanni Astacio-Oquendo
*Assistant Examiner* — Zannatul Ferdous
(74) *Attorney, Agent, or Firm* — Meunier Carlin & Curfman LLC

(57) ABSTRACT

The present disclosure provides a high-frequency magnetoimpedance testing apparatus and method. A testing platform in the apparatus is arranged within a Helmholtz coil and connected to a modulating electric current source and a high-frequency impedance analyzer, respectively; the Helmholtz coil is connected to a DC power source; a processor is connected to the high-frequency impedance analyzer and the DC power source separately; the testing platform includes a first double-sided copper-clad plate, and mode transition switches and connection terminals that are arranged on the first double-sided copper-clad plate; one end of the first double-sided copper-clad plate is connected to the high-frequency impedance analyzer, while the other end of the same is connected to a load; the mode transition switches are connected to the modulating electric current source. The present disclosure can realize in-situ current modulation of metallic fibers and high-frequency magnetoimpedance testing, and improve the testing accuracy.

17 Claims, 4 Drawing Sheets

HIGH-FREQUENCY MAGNETOIMPEDANCE TESTING APPARATUS AND METHOD

PRIORITY

This application claims priority of Chinese patent application number 202011208839.6 filed on Nov. 3, 2020 the contents of which is fully incorporated herein by reference.

TECHNICAL FIELD

The present disclosure relates to the field of magnetoimpedance tests, and more particularly to a high-frequency magnetoimpedance testing apparatus and method.

BACKGROUND

Giant magnetoimpedance (GMI) effect refers to a phenomenon in which the impedance of a magneto-sensitive material changes significantly with the variation of an external magnetic field under alternating current (AC) excitation. Amorphous metallic fibers have a long-range disordered and short-range ordered amorphous structure and a special magnetic domain structure and exhibit excellent properties in mechanics, magnetics, and in particular GMI effect. Currently, the amorphous metallic fibers have received widespread attention from researchers. The amorphous metallic fibers are usually prepared by a deep undercooling rapid solidification technique, where a high cooling rate may result in large residual stress in metallic fibers, stress anisotropy, causing stress anisotropy to become predominant and the GMI effect to be less obvious. This restricts the engineering application of the amorphous metallic fibers as magneto-sensitive materials.

Methods that can effectively reduce the residual stress in the amorphous metallic fibers generally include modulation in vacuum, modulation with a magnetic field, stress modulation, modulation with electrical current, etc. Among those methods, the modulation with electrical current permits generation of Joule heat to reduce the residual stress on the one hand, and control of the surface magnetic domain structure of the amorphous metallic fibers by a toroidal magnetic field generated by the electrical current, thereby providing enhanced GMI effect.

At present, numerous studies have been carried out on the GMI effect of the amorphous metallic fibers, and GMI sensors based on the effect (e.g., stress sensors, magneto-sensitive sensors, and biosensors) have been developed and put into use. However, GMI tests on the amorphous metallic fibers in high frequency band are still not complete enough, and the relevant theoretical research is also not deep enough. Hence, more systematic research will be required. During high-frequency magnetoimpedance testing, it is usually required to frequently solder the metallic fibers for modulation with electrical current, which may affect the testing precision. Therefore, it is desirable to optimize the high-frequency magnetoimpedance testing apparatus and method.

SUMMARY

On this basis, it is necessary to provide a high-frequency magnetoimpedance testing apparatus and method, so solve the problem that the testing accuracy is affected due to repeated soldering of metallic fibers required by modulation annealing with current annealing during magnetoimpedance testing. Besides, it can realize in-situ current modulation of metallic fibers and high-frequency magnetoimpedance testing and improve the testing accuracy.

To achieve the above objective, the present disclosure provides the following solutions:

A high-frequency magnetoimpedance testing apparatus, including: a testing platform, a high-frequency impedance analyzer, a Helmholtz coil, a modulating electric current source, a direct current (DC) power source, and a processor, where the testing platform is arranged within the Helmholtz coil and connected to the modulating electric current source and the high-frequency impedance analyzer, respectively; the Helmholtz coil is connected to the DC power source; the processor is connected to the high-frequency impedance analyzer and the DC power source separately;

the testing platform includes a first double-sided copper-clad plate, mode transition switches, and connection terminals; the mode transition switches and the connection terminals are arranged on the first double-sided copper-clad plate; one end of the first double-sided copper-clad plate is connected to the high-frequency impedance analyzer; the other end of the first double-sided copper-clad plate is connected to a load; the mode transition switches are connected to the modulating electric current source and configured to control the modulating electric current source to be connected and disconnected; the connection terminals are configured to fasten metallic fibers to be tested; and the processor is configured to regulate an output current from the DC power source, so as to control the strength of an external magnetic field generated by the Helmholtz coil, and to obtain magnetoimpedance output characteristics of as-prepared and annealed metallic fibers to be tested.

Optionally, the high-frequency magnetoimpedance testing apparatus further includes: a calibration platform which is configured to calibrate the high-frequency impedance analyzer, where the calibration platform includes a second double-sided copper-clad plate and a calibration kit; one end of the second double-sided copper-clad plate is connected to the high-frequency impedance analyzer, and the other end of the second double-sided copper-clad plate is connected to the calibration kit.

Optionally, the calibration kit includes a circuit breaker, a short circuiter and a load.

Optionally, the high-frequency magnetoimpedance testing apparatus further includes: a uniaxial flux-gate magnetometer, where a probe of the uniaxial flux-gate magnetometer is fixed within the Helmholtz coil and coaxial with the Helmholtz coil; and the uniaxial flux-gate magnetometer is configured to adjust the axis of the Helmholtz coil so that the axis of the Helmholtz coil is perpendicular to the geomagnetic field.

Optionally, the high-frequency magnetoimpedance testing apparatus further includes: a radio-frequency testing connection kit, where the radio-frequency testing connection kit includes an N flat head to SMA adapter, an SMA radio-frequency connecting wire and SMA connectors; one end of the first double-sided copper-clad plate is connected to the high-frequency impedance analyzer orderly through one SMA connector, the SMA radio-frequency connecting wire and the N flat head to SMA adapter; the other end of the first double-sided copper-clad plate is connected to the load through one SMA connector;

one end of the second double-sided copper-clad plate is connected to the high-frequency impedance analyzer orderly through one SMA connector, the SMA radio-frequency connecting wire and the N flat head to SMA adapter; and the other end of the second double-sided copper-clad plate is connected to the calibration kit through one SMA connector.

Optionally, the high-frequency magnetoimpedance testing apparatus further includes: an RS-232C connector and a general purpose interface bus (GPIB), where the DC power source is connected to the processor through the RS-232C connector; and the high-frequency impedance analyzer is connected to the processor through the GPIB.

Optionally, the high-frequency magnetoimpedance testing apparatus further includes: a testing support which is arranged within the Helmholtz coil, where a groove is formed in the testing support to fix the testing platform.

A high-frequency magnetoimpedance testing method for the high-frequency magnetoimpedance testing apparatus described above includes:

adjusting the mode transition switch on the testing platform and controlling the modulating electric current source to be disconnected so that the testing platform is in a high-frequency magnetoimpedance analysis mode of metallic fibers;

obtaining the magnetoimpedance output characteristics of the as-prepared metallic fibers to be tested using a LabVIEW programming-based magnetoimpedance data acquisition program;

adjusting the mode transition switch, controlling the modulating electric current source to be connected so that the testing platform is in an in-situ current modulation mode of metallic fibers, and adjusting output parameters of the modulating electric current source so that the as-prepared metallic fibers to be tested are converted into the annealed metallic fibers to be tested; and obtaining the magnetoimpedance output characteristics of the annealed metallic fibers to be tested using the LabVIEW programming-based magnetoimpedance data acquisition program.

Optionally, before adjusting the mode transition switch on the testing platform and controlling the modulating electric current source to be disconnected so that the testing platform is in a high-frequency magnetoimpedance analysis mode of metallic fibers, the method further includes:

calibrating the high-frequency impedance analyzer using the calibration platform.

Optionally, before calibrating the high-frequency impedance analyzer using the calibration platform, the method further includes:

correcting the magnetic field of Helmholtz coil using the uniaxial flux-gate magnetometer.

Compared with the prior art, the present disclosure has the following beneficial effects:

The present disclosure provides a high-frequency magnetoimpedance testing apparatus and method. The high-frequency magnetoimpedance testing apparatus includes: a testing platform, a high-frequency impedance analyzer, a Helmholtz coil, a modulating electric current source, a direct current (DC) power source, and a processor, where the testing platform is arranged within the Helmholtz coil; the testing platform includes a first double-sided copper-clad plate, and mode transition switches and connection terminals that are arranged on the first double-sided copper-clad plate; one end of the first double-sided copper-clad plate is connected to the high-frequency impedance analyzer, while the other end of the same is connected to a load; the mode transition switches are connected to the modulating electric current source; and the modulating electric current source is regulated to be connected and disconnected, so that the testing platform is in a mode of high-frequency magnetoimpedance analysis of metallic fibers and a mode of in-situ current modulation of metallic fibers, thereby obtaining magnetoimpedance output characteristics of as-prepared and annealed metallic fibers to be tested. The present disclosure can realize modulation with electric current only by adjusting the mode transition switch after obtaining the magnetoimpedance output characteristics of the as-prepared metallic fibers to be tested, thereby realizing in-situ current modulation of metallic fibers and high-frequency magnetoimpedance testing, avoiding repeated removal and soldering of the metallic fibers to be tested and improving the testing accuracy.

BRIEF DESCRIPTION OF THE DRAWINGS

To describe the technical solutions in embodiments of the present disclosure or in the prior art more clearly, the accompanying drawings needed in the embodiments will be introduced below briefly. Apparently, the accompanying drawings in the following description show merely some embodiments of the present disclosure, and other drawings can be derived from these accompanying drawings by those of ordinary skill in the art without creative efforts.

DETAILED DESCRIPTION

The technical solutions in the embodiments of the present disclosure will be described below clearly and completely with reference to the accompanying drawings in the embodiments of the present disclosure. Apparently, the described embodiments are merely a part rather than all of the embodiments of the present disclosure. All other embodiments derived from the embodiments in the present disclosure by those of ordinary skill in the art without creative efforts shall fall within the protection scope of the present disclosure.

To make the foregoing objectives, features, and advantages of the present disclosure clearer and more comprehensible, the present disclosure is further described in detail below in conjunction with the accompanying drawings and specific embodiments.

Figure 1:
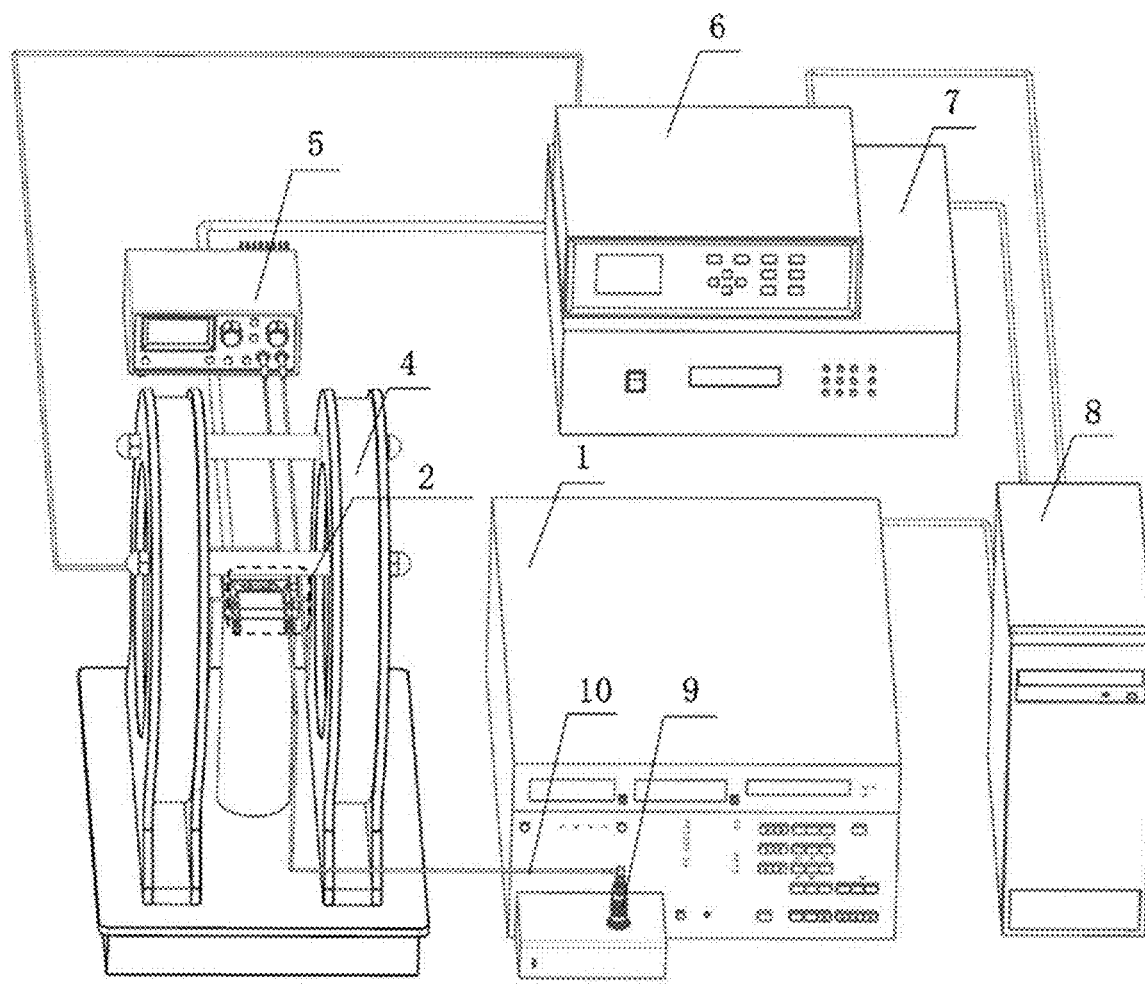
FIG. 1 is a structural schematic diagram of a high-frequency magnetoimpedance testing apparatus according to an embodiment of the present disclosure.

FIG. 1 is a structural schematic diagram of a high-frequency magnetoimpedance testing apparatus according to an embodiment of the present disclosure. Referring to FIG. 1, the high-frequency magnetoimpedance testing apparatus of this embodiment includes: a testing platform 2, a high-frequency impedance analyzer 1, a Helmholtz coil 4, a modulating electric current source 5, a direct current (DC) power source 7, and a processor 8. The testing platform 2 is a platform for in-situ current modulation of metallic fibers and high-frequency magnetoimpedance testing.

The testing platform 2 is arranged within the Helmholtz coil 4. The testing platform 2 is connected to the modulating electric current source 5 and the high-frequency impedance analyzer 1 by means of wires, respectively. The Helmholtz coil 4 is connected to the DC power source 7. The processor 8 is connected to the high-frequency impedance analyzer 1 and the DC power source 7 separately.

Figure 2:
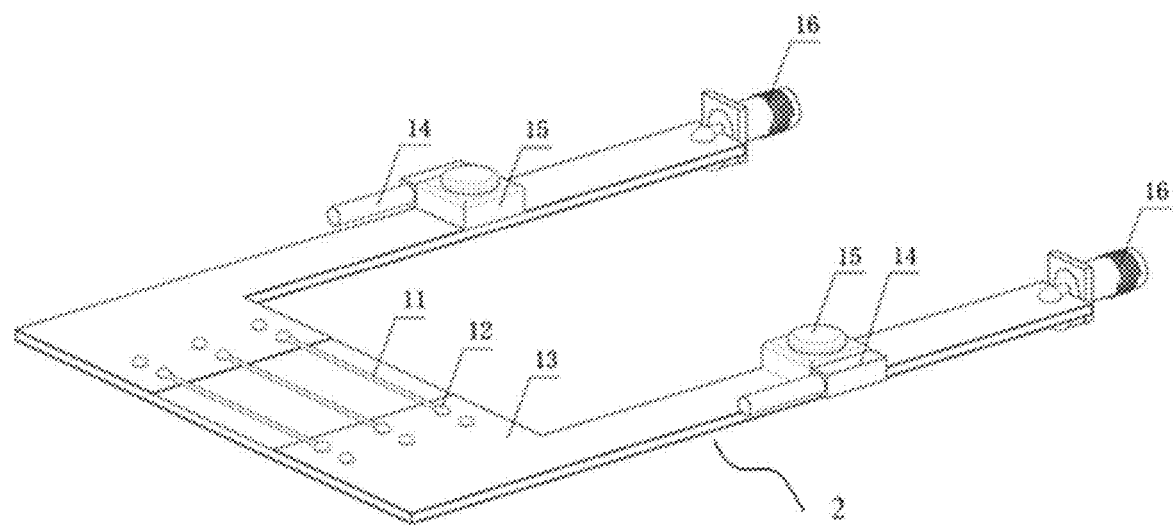
FIG. 2 is a structural schematic diagram of a testing platform according to an embodiment of the present disclosure.

Referring to FIG. 2, the testing platform 2 includes a first double-sided copper-clad plate 13, mode transition switches 15, and connection terminals 12. The mode transition switches 15 and the connection terminals 12 are arranged on the first double-sided copper-clad plate 13. One end of the first double-sided copper-clad plate 13 is connected to the high-frequency impedance analyzer 1. The other end of the first double-sided copper-clad plate 13 is connected to a load 20 (a 50Ω load may be used). The mode transition switches 15 are connected to the modulating electric current source 5 and configured to control the modulating electric current source 5 to be connected and disconnected, thereby realizing transition of a mode of in-situ current modulation of metallic fibers and a mode of high-frequency magnetoimpedance analysis of metallic fibers. The connection terminals 12 are configured to fasten metallic fibers 11 to be tested. Specifically, two mode transition switches 15 are arranged on the first double-sided copper-clad plate 13 and connected to the modulating electric current source 5 by means of corresponding wires 14, respectively. The connection terminals 12 may serve to connect and fasten metallic fibers different in number, diameter and length, and in-situ modulation of the metallic fibers with electrical current can be achieved in the mode of in-situ current modulation of metallic fibers. The modulating electric current source 5 connected to the testing platform 2 can provide DC, AC or electrical currents different in waveform. The high-frequency impedance output characteristics of metallic fibers different in number, diameter and length can be tested and acquired by the high-frequency impedance analyzer 1 and the processor 8 in the mode of high-frequency magnetoimpedance analysis of metallic fibers.

A magnetoimpedance data acquisition system is built in the processor 8. The processor 8 is configured to regulate an output current from the DC power source 7, so as to control the strength of an external magnetic field generated by the Helmholtz coil 4. The Helmholtz coil 4 can provide a maximum external magnetic field of 100 Oe. The processor 8 is further configured to obtain magnetoimpedance output characteristics of as-prepared and annealed metallic fibers 11 to be tested, where the magnetoimpedance output characteristics include a magnetoimpedance change rate and magnetoimpedance response sensitivity.

As an alternative embodiment, the processor 8 may be a computer in which LabVIEW programming-based data acquisition program is built. This program may allow the computer to control the test parameters of the high-frequency impedance analyzer 1 and control the output magnetic field intensity of the Helmholtz coil 4 by controlling the output current value of the DC power source 7. The program has two mode: frequency scanning mode and magnetic field scanning mode and may perform automatic data acquisition and data processing on the magnetoimpedance output characteristics of the metallic fibers 11 to be tested and visually output test results in real time, thereby greatly improving the testing efficiency.

As an alternative embodiment, the model of the high-frequency impedance analyzer 1 may be HP 4191A and its test frequency range f may be 1 MHz to 1000 MHz. The high-frequency impedance analyzer 1 must be preheated for 10 minutes (it must be preheated for 40 minutes for accurate testing) before starting each time, and calibration must be completed before testing.

As an alternative embodiment, there are 12 connection terminals 12 on the testing platform 2, so that test connection of metallic fibers different in length and diameter or parallel to each other can be realized.

Figure 3:
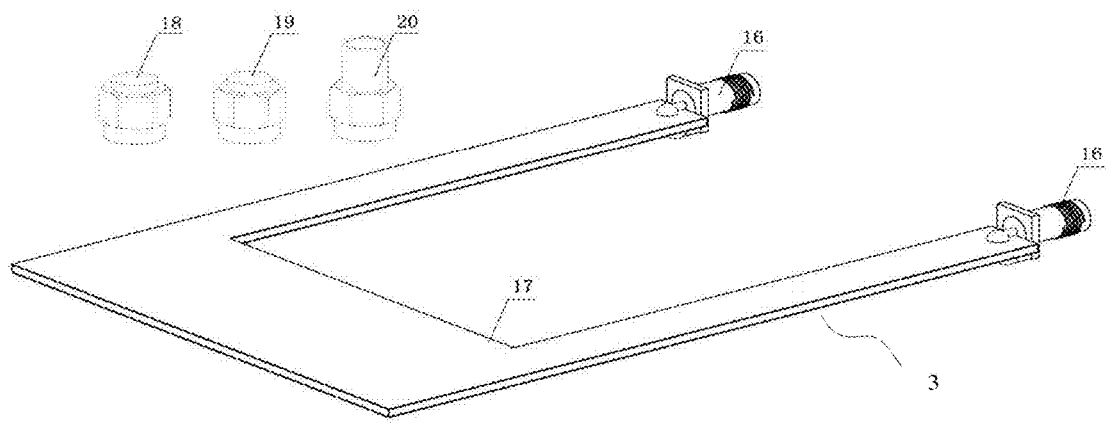
FIG. 3 is a structural schematic diagram of a calibration platform according to an embodiment of the present disclosure.

As an alternative embodiment, the high-frequency magnetoimpedance testing apparatus may further include: a calibration platform 3 which is configured to calibrate the high-frequency impedance analyzer 1 before testing, and in this case, the high-frequency impedance analyzer 1 is switched to a "calibration mode". Referring to FIG. 3, the calibration platform 3 includes a second double-sided copper-clad plate 17 and a calibration kit. One end of the second double-sided copper-clad plate 17 is connected to the high-frequency impedance analyzer 1, and the other end of the second double-sided copper-clad plate 17 is connected to the calibration kit. The calibration platform 3 may be a magnetoimpedance testing calibration platform 3.

As an alternative embodiment, the calibration kit may be an SMA calibration kit. The calibration kit may include a circuit breaker 18, a short circuiter 19 and a load 20. The load 20 may be a 50Ω load.

As an alternative embodiment, the high-frequency magnetoimpedance testing apparatus may further include: a uniaxial flux-gate magnetometer 6. A probe of the uniaxial flux-gate magnetometer 6 may be fixed within the Helmholtz coil 4 and coaxial with the Helmholtz coil 4. The uniaxial flux-gate magnetometer 6 is configured to adjust the axis of the Helmholtz coil 4 so that the axis of the Helmholtz coil 4 is perpendicular to the geomagnetic field. Thus, the geomagnetic field can be avoided from influencing the magnetoimpedance testing by using the high-sensitivity uniaxial flux-gate magnetometer 6 to adjust the axis of the Helmholtz coil 4 to be perpendicular to the geomagnetic field. The uniaxial flux-gate magnetometer 6 may also be connected to the processor 8.

As an alternative embodiment, the high-frequency magnetoimpedance testing apparatus may further include: a radio-frequency testing connection kit. An input end of the testing platform 2 and an output end of the high-frequency impedance analyzer 1 are connected by means of the radio-frequency testing connection kit and fixed in a groove of an internal support of the Helmholtz coil 4. The radio-frequency testing connection kit includes an N flat head to SMA adapter 9, an SMA radio-frequency connecting wire 10 and 4 SMA connectors 16. One end of the first double-sided copper-clad plate 13 is connected to the high-frequency impedance analyzer 1 orderly through one SMA connector 16, the SMA radio-frequency connecting wire 10 and the N flat head to SMA adapter 9. The other end of the first double-sided copper-clad plate 13 is connected to the load 20 through one SMA connector 16.

One end of the second double-sided copper-clad plate 17 in the calibration platform 3 is connected to the high-frequency impedance analyzer 1 orderly through one SMA connector 16, the SMA radio-frequency connecting wire 10 and the N flat head to SMA adapter 9. The other end of the second double-sided copper-clad plate 17 is connected to the calibration kit through one SMA connector 16. During calibration, the other end of the second double-sided copper-clad plate 17 is successively connected to the circuit breaker 18, the short circuiter 19 and the load 20 through one SMA connector 16, so that the calibration of the high-frequency impedance analyzer 1 can be completed using different devices.

The error caused by the connecting wire during testing can be reduced when the radio-frequency testing connection kit is used for the testing platform 2 or the calibration platform 3.

As an alternative embodiment, the high-frequency magnetoimpedance testing apparatus may further include: an RS-232C connector and a general purpose interface bus (GPIB). The DC power source 7 is connected to the processor 8 through the RS-232C connector. The high-frequency impedance analyzer 1 is connected to the processor 8 through the GPIB.

As an alternative embodiment, the high-frequency magnetoimpedance testing apparatus may further include: a testing support which is arranged within the Helmholtz coil 4. A groove is formed in the testing support to fix the testing platform 2, thereby guaranteeing that the positions of the metallic fibers 11 to be tested are not changed during testing. Moreover, the testing support may further fix the probe of the uniaxial flux-gate magnetometer 6, and the probe is coaxial with the Helmholtz coil 4.

Figure 4:
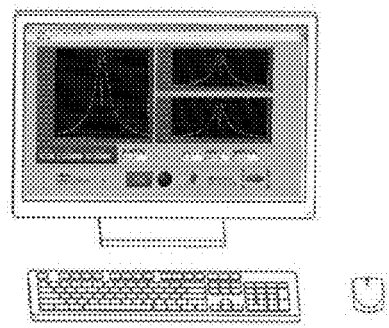
FIG. 4 is a structural schematic diagram of a displayer according to an embodiment of the present disclosure.

As an alternative embodiment, the apparatus may further include: a displayer which is connected to the processor 8, as shown in FIG. 4.

The high-frequency magnetoimpedance testing apparatus in this embodiment firstly calibrates the high-frequency impedance analyzer 1 using the calibration platform 3 and corrects the magnetic field of the Helmholtz coil 4 using the uniaxial flux-gate magnetometer 6. Then, the testing platform 2 on which the as-prepared metallic fibers are fastened is fixed to the internal support of the Helmholtz coil 4, and then magnetoimpedance testing is carried out to obtain the high-frequency impedance output characteristics of the as-prepared metallic fibers. The mode transition switch 15 is adjusted to the in-situ modulation mode of metallic fibers, and the output current of the modulating electric current source 5 is adjusted for in-situ modulation with electric current. The mode transition switch 15 is adjusted to the high-frequency magnetoimpedance analysis mode of metallic fibers for magnetoimpedance testing, thereby obtaining the high-frequency magnetoimpedance output characteristics of the modulated annealed metallic fibers. The apparatus realizes in-situ current modulation of metallic fibers and high-frequency magnetoimpedance testing.

The present disclosure further provides a high-frequency magnetoimpedance testing method for use on the above described high-frequency magnetoimpedance testing apparatus. The method includes the following steps:

Correct the magnetic field of the Helmholtz coil 4 using the uniaxial flux-gate magnetometer 6.

Calibrate the high-frequency impedance analyzer 1 using the calibration platform 3.

Adjust the mode transition switch 15 on the testing platform 2 and control the modulating electric current source 5 to be disconnected so that the testing platform 2 is in a high-frequency magnetoimpedance analysis mode of metallic fibers. Obtain the magnetoimpedance output characteristics of the as-prepared metallic fibers 11 to be tested using the LabVIEW programming-based magnetoimpedance data acquisition program.

Adjust the mode transition switch 15, control the modulating electric current source 5 to be connected so that the testing platform 2 is in the in-situ modulation mode of metallic fibers with electric current, and adjust the output parameters of the modulating electric current source 5 so that the as-prepared metallic fibers 11 to be tested are converted into the annealed metallic fibers 11 to be tested; and obtain the magnetoimpedance output characteristics of the annealed metallic fibers 11 to be tested using the LabVIEW programming-based magnetoimpedance data acquisition program.

In actual application, the high-frequency magnetoimpedance testing method for use on the high-frequency magnetoimpedance testing apparatus specifically includes the following steps:

The first step, magnetic field correction: the Helmholtz coil 4 was placed perpendicular to the direction of the geomagnetic field, thereby avoiding the interference of the geomagnetic field. The probe of the uniaxial flux-gate magnetometer 6 is firstly fixed in the Helmholtz coil 4 in the axial direction of the Helmholtz coil 4, and meanwhile, the position of the probe of the uniaxial flux-gate magnetometer 6 is coaxial with the Helmholtz coil 4. The position of the Helmholtz coil 4 is adjusted so that the uniaxial flux-gate magnetometer 6 displays the magnetic field as 0 T, thereby completing zero magnetic field correction. The DC power source 7 is turned on and the data acquisition program of the processor 8 is initiated to set frequency scanning at 10 e magnetic field. The difference between the reading of the uniaxial flux-gate magnetometer 6 and a set value is observed, and the two values may be approximated to each other by adjusting a magnetic field transformation coefficient in the data acquisition program, thereby completing the magnetic field correction.

The second step, testing target placement: the metallic fibers 11 to be tested are fixed to the connection terminals 12 of the testing platform 2 that are fixed in the groove of the internal support of the Helmholtz coil 4, guaranteeing that the metallic fibers 11 to be tested are coaxial with the Helmholtz coil 4.

The third step, calibration of the high-frequency impedance analyzer 1: the high-frequency impedance analyzer 1 is turned on and must be preheated for 10 minutes (it must be preheated for 40 minutes for accurate testing). The high-frequency impedance analyzer 1 is connected to the calibration platform 3 using the SMA radio-frequency connecting wire 10, and calibrated orderly using the circuit breaker 18, the short circuiter 19 and the 50Ω load. After the calibration is completed, the calibration platform 3 is removed, and the high-frequency impedance analyzer 1 is connected to the testing platform 2 using the SMA radio-frequency connecting wire 10.

The fourth step, the mode transition switch 15 on the testing platform 2 is adjusted to the high-frequency magnetoimpedance analysis mode of metallic fibers. The SMA connector 16 at an end of the test platform 2 is connected to the 50Ω load, and the high-frequency magnetoimpedance output characteristics of the as-prepared metallic fibers are obtained and analyzed by means of the LabVIEW programming-based data acquisition program, where the analysis approach for the influence rule is as follows:

magnetoimpedance change $$\text{rate: } \Delta Z / Z_{max}(\%) = \left[ \frac{Z(H_{ex}) - Z(H_{max})}{Z(H_{max})} \right] \times 100\%;$$

-continued

Magnetic field response sensitivity: $\xi(\%/Oe) = \dfrac{d[\Delta Z/Z_{max}]}{dH_{ex}}$;

where $\Delta Z$ is a difference between the impedance at a different external magnetic field and the impedance at the maximum external magnetic field; $Z_{max}$ is the impedance value at the maximum external magnetic field; $Z(H_{ex})$ is the impedance value at a certain external magnetic field $H_{ex}$; and $Z(H_{max})$ is the impedance value at the maximum external magnetic field.

The fifth step, in-situ current modulation of metallic fibers: the mode transition switch 15 on the testing platform 2 is adjusted to the in-situ modulation mode of metallic fibers with electric current, and the modulating electric current source 5 is capable of modulating the metallic fibers with electric currents different in intensity and type.

The sixth step, the mode transition switch 15 on the testing platform 2 is adjusted to the high-frequency magnetoimpedance analysis mode of metallic fibers, and the high-frequency magnetoimpedance output characteristics of the annealed metallic fibers modulated with electric current are obtained and analyzed by means of the LabVIEW programming-based data acquisition program.

Figure 5:
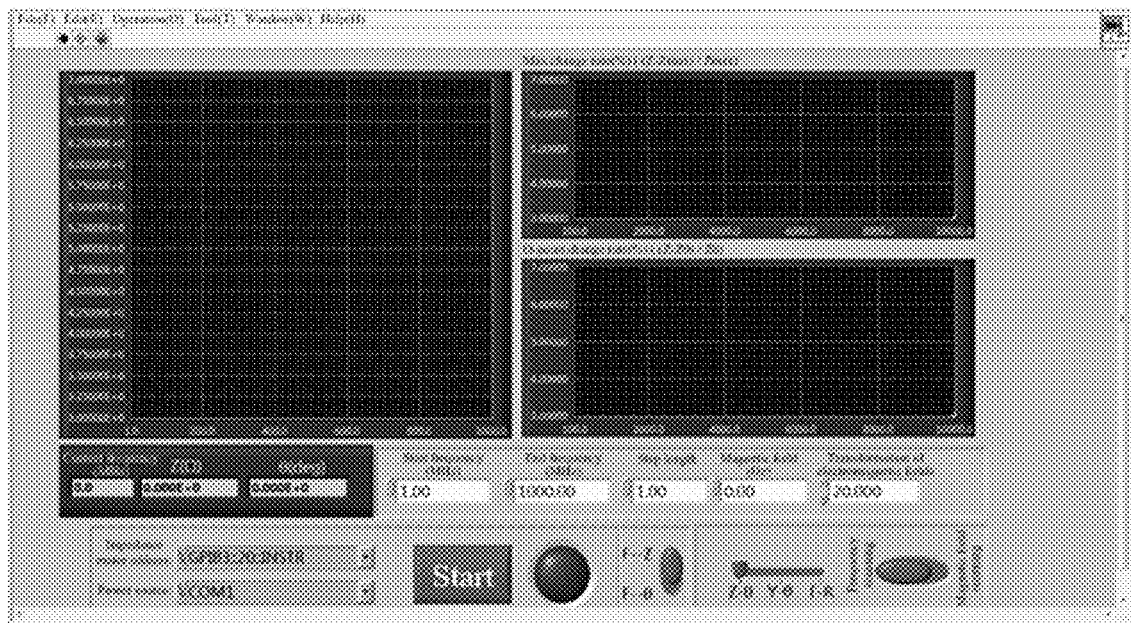
FIG. 5 is an interface diagram of LabVIEW programming-based data acquisition program in a frequency scanning mode according to an embodiment of the present disclosure.
Figure 6:
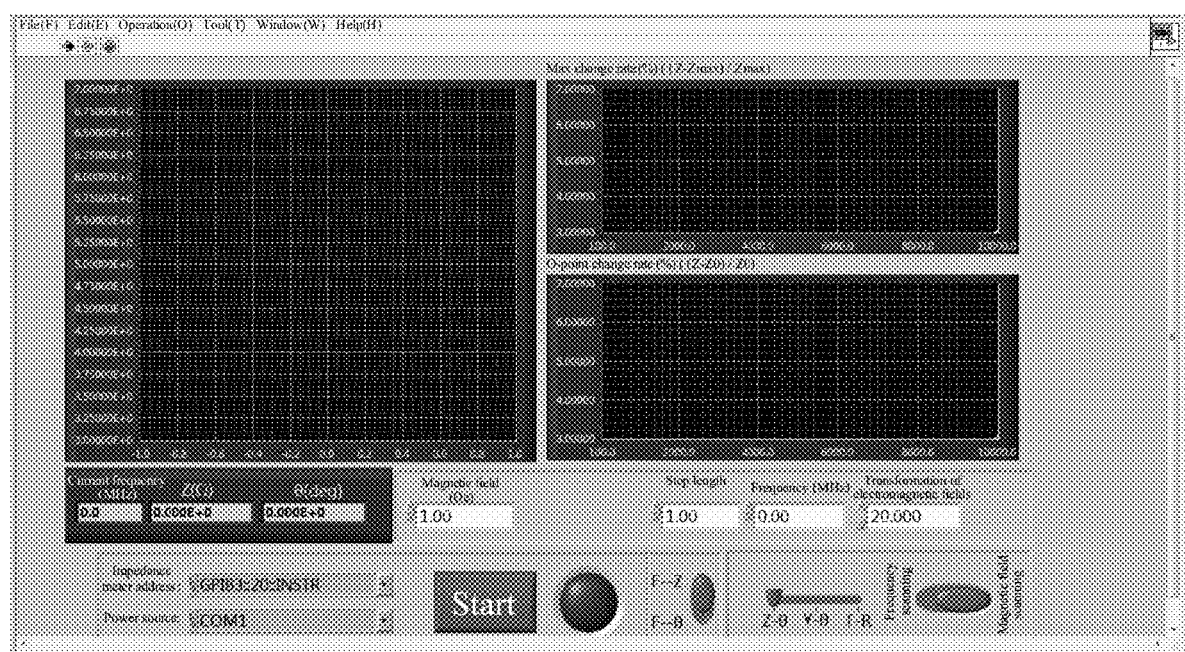
FIG. 6 is an interface diagram of LabVIEW programming-based data acquisition program in a magnetic field scanning mode according to an embodiment of the present disclosure.

The data acquisition program includes a frequency scanning mode and a magnetic field scanning mode. The frequency scanning mode may be used to acquire the impedance output characteristics of the metallic fibers at different frequencies under a magnetic field intensity. The magnetic field scanning mode may be used to acquire the impedance output characteristics of the metallic fibers at a frequency under different magnetic field intensities. Moreover, the data acquisition program may display the acquired or calculated data on the interface of the software in the form of a line chart in real time. The interface of the frequency scanning mode of the LabVIEW programming-based data acquisition program is as shown in FIG. 5, and the interface of the magnetic field scanning mode of the LabVIEW programming-based data acquisition program is as shown in FIG. 6.

Figure 7:
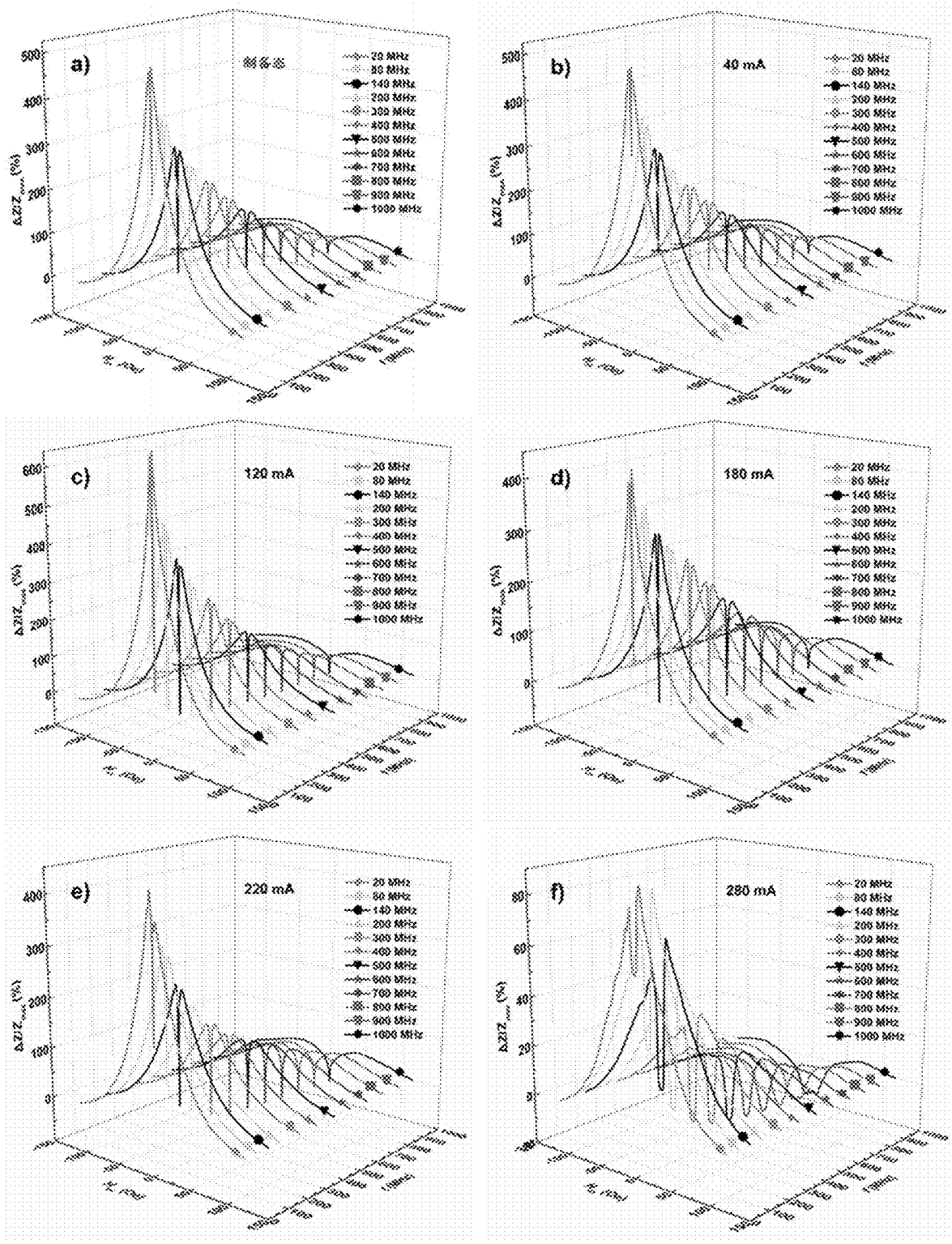
FIG. 7 shows GMI high-frequency characteristic curve charts of metallic fibers before and after being modulated with electrical current.

There is provided a more specific example below in combination with the high-frequency magnetoimpedance testing apparatus and the high-frequency magnetoimpedance testing method provided by the above embodiments, and the effects of the example are explained in conjunction with specific test results. At a testing frequency of 20 MHz to 1000 MHz and within an external magnetic field scanning range of −100 Oe to 100 Oe, the magnetoimpedance output characteristics of the as-prepared metallic fibers and the annealed metallic fibers with electric currents of 40 mA, 120 mA, 180 mA, 220 mA and 280 mA were tested, respectively. The GMI high-frequency characteristic curves of the metallic fibers before and after modulation with electric current are as shown in FIG. 7, where FIG. 7 a) is the GMI high-frequency characteristic curves of the as-prepared metallic fibers, while FIG. 7 b) the GMI high-frequency characteristic curves of the annealed metallic fibers with electric current of 40 mA, FIG. 7 c) the GMI high-frequency characteristic curves of the annealed metallic fibers with electric current of 120 mA, FIG. 7 d) the GMI high-frequency characteristic curves of the annealed metallic fibers with electric current of 180 mA, FIG. 7 e) the GMI high-frequency characteristic curves of the annealed metallic fibers with electric current of 220 mA, and FIG. 7 f) the GMI high-frequency characteristic curves of the annealed metallic fibers with electric current of 280 mA. As shown in FIG. 7, the values of $[\Delta Z/Z_{max}]_{max}$ of the as-prepared metallic fibers and the annealed metallic fibers with electric currents of 40 mA, 120 mA, 180 mA and 220 mA decreased with increasing frequency f, and the value of $[\Delta Z/Z_{max}]_{max}$ of the annealed metallic fibers with electric current of 280 mA was in a trend of increasing first and then decreasing with increasing frequency f. The values of maximum $[\Delta Z/Z_{max}]_{max}$ before and after electric current annealing was in a trend of increasing first and then decreasing with increasing electric current annealing intensity, which were 505.21%, 508.13%, 678.70%, 452.16%, 437.73% and 92.49%, respectively. When f=20 MHz, the $[\Delta Z/Z_{max}]_{max}$ of the annealed metallic fibers with electric current of 120 mA was maximum, namely 678.70%. Therefore, the GMI effect of the metallic fibers can be improved through modulation annealing with electric current of a moderate intensity.

The high-frequency magnetoimpedance testing apparatus of the present disclosure is a high-frequency magnetoimpedance testing apparatus based on in-situ current modulation of metallic fibers, which is an apparatus capable of in-situ modulation annealing of metallic fibers with electric current and high-frequency magnetoimpedance testing and solves the problem that the testing accuracy is affected due to repeated soldering of metallic fibers required by modulation annealing with current annealing during magnetoimpedance testing. Moreover, the apparatus of the present disclosure is rich in functions, simple and practicable. The LabVIEW programming-based magnetoimpedance testing system realizes automatic and visual high-frequency magnetoimpedance testing, greatly improves the efficiency and accuracy of testing, and provides technical support for further research on high-frequency magnetoimpedance characteristics of metallic fibers.

Different embodiments of this specification are described in a progressive manner. The description of each embodiment focuses on the differences from other embodiment, and mutual reference may be made to the same and similar parts of different embodiments.

Specific examples are used herein for illustration of the principles and embodiments of the present disclosure. The description of the foregoing embodiments is used to help illustrate the method of the present disclosure and the core principles thereof. In addition, those of ordinary skill in the art can make various modifications in terms of specific embodiments and scope of application in accordance with the teachings of the present disclosure. In conclusion, the content of the present specification shall not be construed as limitations to the present disclosure.

What is claimed is:

1. A high-frequency magnetoimpedance testing apparatus, comprising: a testing platform, a high-frequency impedance analyzer, a Helmholtz coil, a modulating electric current source, a direct current (DC) power source, and a processor, wherein
the testing platform is arranged within the Helmholtz coil and connected to the modulating electric current source and the high-frequency impedance analyzer, respectively; the Helmholtz coil is connected to the DC power source; the processor is connected to the high-frequency impedance analyzer and the DC power source separately;
the testing platform comprises a first double-sided copper-clad plate, mode transition switches, and connection terminals; the mode transition switches and the connection terminals are arranged on the first double-sided copper-clad plate; one end of the first double-sided copper-clad plate is connected to the high-frequency impedance analyzer; the other end of the first double-sided copper-clad plate is connected to a load; the mode transition switches are connected to the modulating electric current source and configured to control the modulating electric current source to be connected and disconnected; the connection terminals are configured to fasten metallic fibers to be tested; and the processor is configured to regulate an output current from the DC power source, so as to control the strength of an external magnetic field generated by the Helmholtz coil, and to obtain magnetoimpedance output characteristics of as-prepared and annealed metallic fibers to be tested.

2. The high-frequency magnetoimpedance testing apparatus according to claim 1, further comprising: a calibration platform which is configured to calibrate the high-frequency impedance analyzer, wherein the calibration platform comprises a second double-sided copper-clad plate and a calibration kit; one end of the second double-sided copper-clad plate is connected to the high-frequency impedance analyzer, and the other end of the second double-sided copper-clad plate is connected to the calibration kit.

3. The high-frequency magnetoimpedance testing apparatus according to claim 2, wherein the calibration kit comprises a circuit breaker, a short circuiter and a load.

4. The high-frequency magnetoimpedance testing apparatus according to claim 1, further comprising: a uniaxial flux-gate magnetometer, wherein a probe of the uniaxial flux-gate magnetometer is fixed within the Helmholtz coil and coaxial with the Helmholtz coil; and the uniaxial flux-gate magnetometer is configured to adjust the axis of the Helmholtz coil so that the axis of the Helmholtz coil is perpendicular to the geomagnetic field.

5. The high-frequency magnetoimpedance testing apparatus according to claim 1, further comprising: an RS-232C connector and a general purpose interface bus (GPIB), wherein the DC power source is connected to the processor through the RS-232C connector; and the high-frequency impedance analyzer is connected to the processor through the GPIB.

6. The high-frequency magnetoimpedance testing apparatus according to claim 1, further comprising: a testing support which is arranged within the Helmholtz coil, wherein a groove is formed in the testing support to fix the testing platform.

7. A high-frequency magnetoimpedance testing method for the high-frequency magnetoimpedance testing apparatus according to claim 1, the method comprising:

adjusting the mode transition switches on the testing platform and controlling the modulating electric current source to be disconnected so that the testing platform is in a high-frequency magnetoimpedance analysis mode of metallic fibers;

obtaining the magnetoimpedance output characteristics of the as-prepared metallic fibers to be tested;

using a LabVIEW programming-based magnetoimpedance data acquisition program;

adjusting the mode transition switches, controlling the modulating electric current source to be connected so that the testing platform is in an in-situ current modulation mode of metallic fibers, and adjusting output parameters of the modulating electric current source so that the as-prepared metallic fibers to be tested are converted into the annealed metallic fibers to be tested; and obtaining the magnetoimpedance output characteristics of the annealed metallic fibers to be tested using the LabVIEW programming-based magnetoimpedance data acquisition program(,) and using the obtained magneto-impedance output characteristics of the annealed metallic fibers to solve a problem that testing accuracy is affected due to repeated soldering of metallic fibers required by modulation annealing with current annealing during magnetoimpedance testing.

8. The high-frequency magnetoimpedance testing method according to claim 7, further comprising: a calibration platform which is configured to calibrate the high-frequency impedance analyzer, wherein the calibration platform comprises a second double-sided copper-clad plate and a calibration kit; one end of the second double-sided copper-clad plate is connected to the high-frequency impedance analyzer, and the other end of the second double-sided copper-clad plate is connected to the calibration kit.

9. The high-frequency magnetoimpedance testing method according to claim 8, wherein the calibration kit comprises a circuit breaker, a short circuiter and a load.

10. The high-frequency magnetoimpedance testing method according to claim 9, wherein before adjusting the mode transition switch switches on the testing platform and controlling the modulating electric current source to be disconnected so that the testing platform is in a high-frequency magnetoimpedance analysis mode of metallic fibers, the method further comprises: calibrating the high-frequency impedance analyzer using the calibration platform.

11. The high-frequency magnetoimpedance testing method according to claim 8, wherein before adjusting the mode transition switches on the testing platform and controlling the modulating electric current source to be disconnected so that the testing platform is in a high-frequency magnetoimpedance analysis mode of metallic fibers, the method further comprises: calibrating the high-frequency impedance analyzer using the calibration platform.

12. The high-frequency magnetoimpedance testing method according to claim 7, further comprising: a uniaxial flux-gate magnetometer, wherein a probe of the uniaxial flux-gate magnetometer is fixed within the Helmholtz coil and coaxial with the Helmholtz coil; and the uniaxial flux-gate magnetometer is configured to adjust the axis of the Helmholtz coil so that the axis of the Helmholtz coil is perpendicular to the geomagnetic field.

13. The high-frequency magnetoimpedance testing method according to claim 12, wherein before adjusting the mode transition switches on the testing platform and controlling the modulating electric current source to be disconnected so that the testing platform is in a high-frequency magnetoimpedance analysis mode of metallic fibers, the method further comprises: calibrating the high-frequency impedance analyzer using the calibration platform.

14. The high-frequency magnetoimpedance testing method according to claim 7, further comprising: an RS-232C connector and a general purpose interface bus (GPIB), wherein the DC power source is connected to the processor through the RS-232C connector; and the high-frequency impedance analyzer is connected to the processor through the GPIB.

15. The high-frequency magnetoimpedance testing method according to claim 7, further comprising: a testing support which is arranged within the Helmholtz coil, wherein a groove is formed in the testing support to fix the testing platform.

16. The high-frequency magnetoimpedance testing method according to claim 7, wherein before adjusting the mode transition switches on the testing platform and controlling the modulating electric current source to be disconnected so that the testing platform is in a high-frequency magnetoimpedance analysis mode of metallic fibers, the method further comprises: calibrating the high-frequency impedance analyzer using the calibration platform.

17. The high-frequency magnetoimpedance testing method according to claim 16, before calibrating the high-frequency impedance analyzer using the calibration platform, the method further comprises:

correcting the magnetic field of Helmholtz coil using a uniaxial flux-gate magnetometer.

* * * * *